US00PP31125P3

(12) United States Plant Patent
Wang

(10) Patent No.: US PP31,125 P3
(45) Date of Patent: Nov. 26, 2019

(54) ***LYCIUM* PLANT NAMED 'FPW07'**

(50) Latin Name: *Lycium barbarum*
Varietal Denomination: FPW07

(71) Applicant: Wencai Wang, Angers (FR)

(72) Inventor: Wencai Wang, Angers (FR)

(73) Assignee: FPW Developpment S.A.S. (FR)

( * ) Notice: Subject to any disclaimer, the term of this patent is extended or adjusted under 35 U.S.C. 154(b) by 0 days.

(21) Appl. No.: 15/932,142

(22) Filed: Feb. 9, 2018

(65) Prior Publication Data

US 2018/0242492 P1 Aug. 23, 2018

(30) Foreign Application Priority Data

Feb. 17, 2017 (QZ) ..... PBR 20170469

(51) Int. Cl.
*A01H 5/02* (2018.01)
*A01H 6/82* (2018.01)

(52) U.S. Cl.
USPC ..... Plt./258
CPC ..... *A01H 6/82* (2018.05)

(58) Field of Classification Search
USPC ..... Plt./258
CPC ..... A01H 5/08
See application file for complete search history.

*Primary Examiner* — Keith O. Robinson
(74) *Attorney, Agent, or Firm* — Cassandra Bright

(57) ABSTRACT

A new and distinct *Lycium barbarum* cultivar named 'FPW07' is disclosed, characterized by heavy production of large, orange-red fruit. The new variety bears fruit in the Spring and again in late Summer to early Fall. Fruits are larger and less astringent in taste than known Goji berry varieties. The new variety is suitable for commercial fruit production purposes.

2 Drawing Sheets

Latin name of the genus and species: *Lycium barbarum.*
Variety denomination: 'FPW07'.

BACKGROUND OF THE INVENTION

The new cultivar is a product of a planned breeding program at a research nursery in Anjou, France. Seed was bulk collected from various *Lycium barbarum* varieties produced by open-pollination and grown out for testing. The exact parent varieties cannot be identified. The open-pollination resulting in 'FPW07' was made during 2013.

Plants of the new variety were first selected during 2015. Fruit of the new variety was evaluated with favorable results and plants were found to have a more controlled habit. First asexual propagation occurred at a research nursery in Anjou, France using dormant hardwood cuttings. Subsequent evaluations of the variety have shown the characteristics to be true to type.

SUMMARY OF THE INVENTION

The cultivar 'FPW07' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FPW07'. These characteristics in combination distinguish 'FPW07' as a new and distinct *Lycium barbarum* cultivar:

1. Red to dark orange berries.
2. Purple flowers.
3. Large fruit.
4. Dark green foliage.
5. Strong plant resistance to heat and wind.
6. Fruit with a lower astringency.

COMMERCIAL COMPARISON

The new variety can be compared to the commercial variety *Lycium barbarum* 'Big', unpatented. The cultivars are similar in most horticultural characteristics, however the new variety differs in the following:

1. New variety bears larger fruit than that of this comparator.
2. New variety has darker green leaves than this comparator.

The new variety can be compared to the commercial variety *Lycium barbarum* 'FPW03', filed concurrently and having application Ser. No. 15/932,143. The cultivars are similar in most horticultural characteristics, however, the new variety differs in the following:

1. 'FPW07' bears smaller fruit than 'FPW03'.
2. 'FPW07' grows faster and more vigorously than 'FPW03'.
3. 'FPW07' bears more fruit per plant than 'FPW03'.

BRIEF DESCRIPTION OF THE PHOTOGRAPHS

Figure 1:
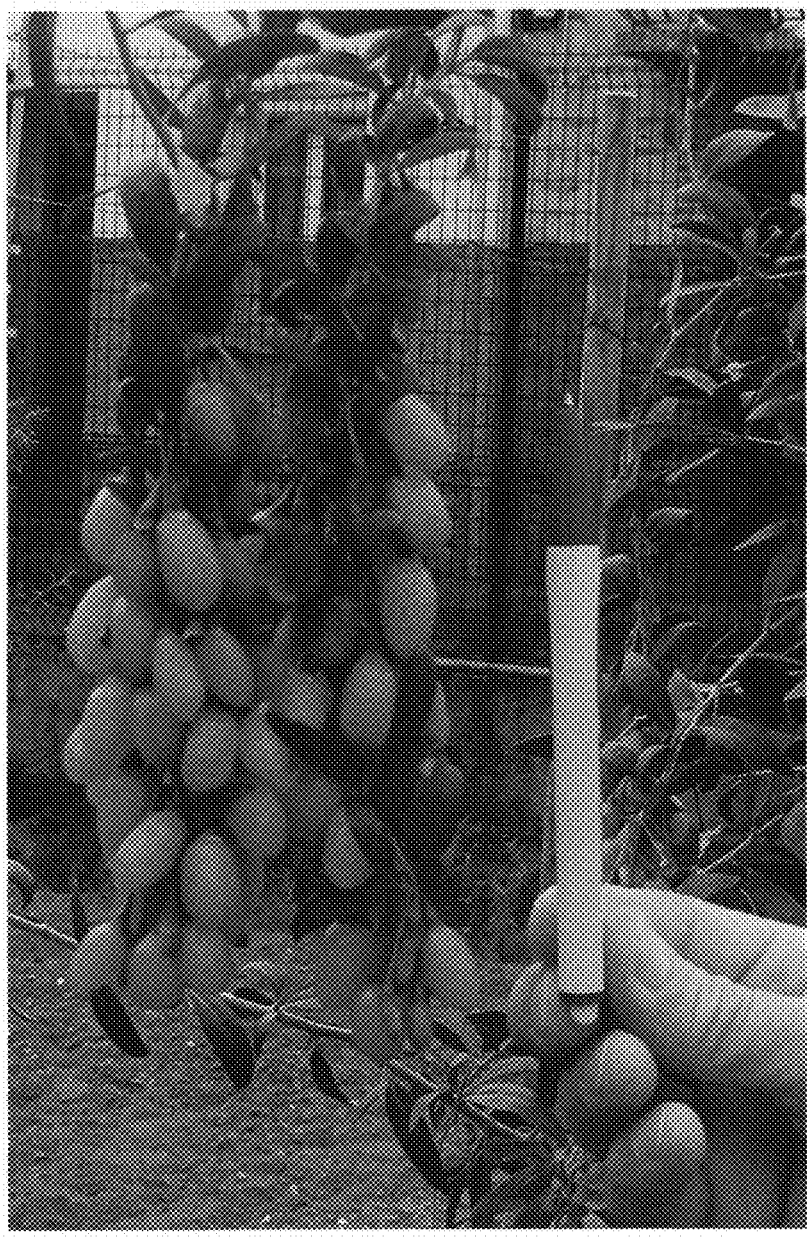

The accompanying photograph in FIG. 1 illustrates in full color examples of typical fruits of 'FPW07', while on the plant, as well as typical foliage. This figure illustrates the heavy bearing characteristics of the variety.

Figure 2:
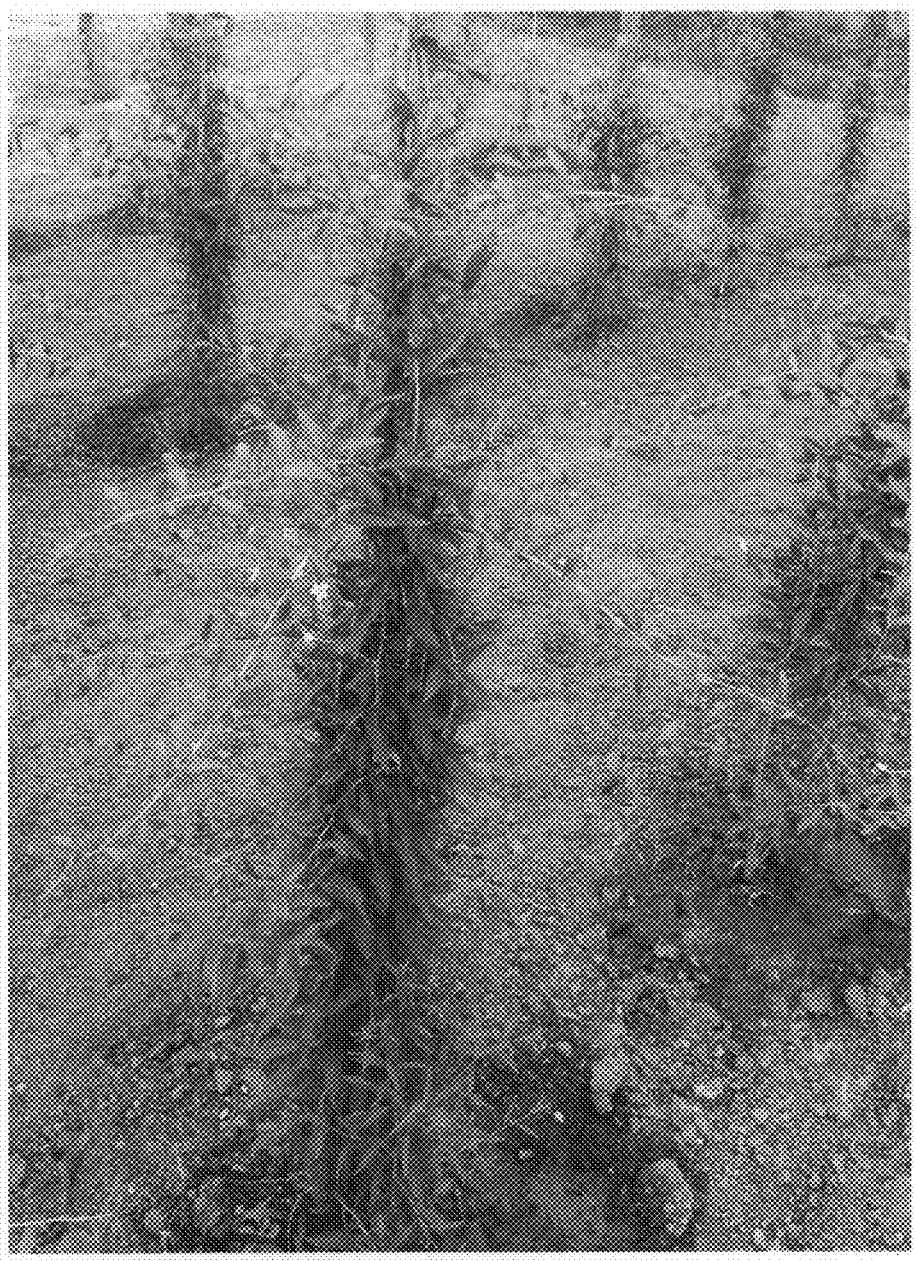

FIG. 2 illustrates a plant of 'FPW07' at approximately 6 to 8 months of age, planted in the ground in Revel, France.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'FPW07' plants grown outdoors in Camarillo, Calif. The growing temperature ranged from about 15° C. to 33° C. during the day and 5° C. to 15° C. at night. Measurements and numerical values represent an average of typical plant types, measurements of foliage taken from mid June to mid August. Fruit was measured in April and again in August.

Botanical classification: *Lycium barbarum* 'FPW07'.

Propagation: Typical propagation is by fresh softwood cuttings in Spring. Hardwood cuttings can be rooted as well, with a lower success rate.

*Rooting habit.*—Woody to semi-woody. Moderately well branched, colored near Brown 200B.

Plant:

*Age of the plant described.*—About 1.5 years from a rooted plantlet.

*Average height.*—About 2 meters.

*Average width.*—About 1 to 1.5 meters.

*Vigor.*—Moderate.

*Young shoot color.*—Near RHS Yellow-Green 144B.

*Young shoot texture.*—Glabrous, with a few striations.

*Mature branch color.*—Greyed-Green 195B.

*Mature branch/shoot diameter.*—Average 5 to 7 mm.

*Mature branch/shoot length.*—1 to 2 meters, depending upon pruning.

*Mature branch/shoot texture.*—Glabrous, some ridges, very slightly glaucous. Thorns.

*Thorn description.*—Length: Broad range, 5 to 40 mm. Width at base: 2 mm. Shape: Needlelike.

*Density.*—Spaced about 1.5 to 2.0 cm apart on stem.

Foliage:

Leaf:

*Average length.*—7 to 10 cm.

*Average width.*—1.2 cm.

*Shape of blade.*—Elliptic.

*Apex.*—Acute.

*Base.*—Tapered.

*Attachment.*—Sessile or reduced petiole.

*Margin.*—Entire.

*Texture of top surface.*—Glabrous.

*Texture of under side.*—Glabrous.

*Color.*—Mature foliage upper side: Green N137A. Mature foliage under side: Yellow-Green 147A.

*Petiole.*—Length: 4 to 8 mm. Diameter: 3 mm. Texture: Glabrous. Color: Near Yellow-Green 144C.

Flower:

*Bud color.*—Purple 77A to 77B and Yellow-White 158B.

*Bud shape.*—Oval.

*Diameter.*—About 5 mm.

*Length.*—About 8 mm.

*Petal quantity.*—5 per flower.

*Petals overlapping.*—Slightly.

*Petals.*—Length: 9 mm. Width: 4 mm. Shape: Deltate. Aspect: Curved backward. Margin: Entire. Texture: Glabrous, all surfaces. Base: Fused. Apex: Acute.

*Petals color.*—Upper Surface: Purple 77A, margin near 76D. Lower Surface: Near Purple 75D.

*Sepals.*—Number of Sepals: 5, fused. Color of Sepals: Green 138C. Sepal Width: 3 mm. Sepal Length: 5 mm. Sepal Texture: Glabrous. Sepal shape: Deltate, fused over 50%. Sepal Margin: Entire. Sepal Apex: Acute. Sepal Base: Fused.

Peduncle:

*Length.*—2 to 5 cm.

*Diameter.*—2 mm.

*Color.*—Near Yellow-Green 144D.

*Texture.*—Glabrous.

Fruit:

*Average length.*—1.6 cm.

*Average diameter.*—1.2 cm.

*Color.*—Near Orange-Red N34B.

*General shape.*—Varying, slightly irregular elongated oval.

*Average weight.*—0.5 grams to 0.8 grams.

*Firmness.*—Soft.

*Flavor profile.*—Low astringent, semi-sweet.

*Fragrance.*—Faint fresh/sweet scent.

*Seeds.*—Average 15 to 20, flat, less than 1 mm in diameter. Colored near Yellow-White 158A.

*Fruit peduncle length.*—2 to 4.5 cm.

*Fruit peduncle width.*—2 mm.

*Harvest time.*—Spring and again in Late Summer to Early Fall under California conditions.

Other characteristics:

Storage life: Storage life is about 2 to 3 weeks when stored at 2° C.

Disease/pest resistance: Powdery mildew resistant, assumed pathogen is *Arthrocladiella*.

Temperature tolerance: Tolerates low temperatures to approximately −5° C. without negative effects, tolerates high temperatures to approximately 35° C. without negative effects.

What is claimed is:

1. A new and distinct cultivar of *Lycium barbarum* plant named 'FPW07' as herein illustrated and described.

* * * * *